United States Patent [19]

Baldwin

[11] 4,058,614

[45] Nov. 15, 1977

[54] SUBSTITUTED IMIDAZOLE COMPOUNDS AND THERAPEUTIC COMPOSITIONS THEREWITH

[75] Inventor: John J. Baldwin, Lansdale, Pa.

[73] Assignee: Merck & Co., Inc., Rahway, N.J.

[21] Appl. No.: 658,955

[22] Filed: Feb. 18, 1976

Related U.S. Application Data

[63] Continuation of Ser. No. 421,553, Dec. 4, 1973, abandoned.

[51] Int. Cl.² .................. A61K 31/415; C07D 403/02
[52] U.S. Cl. ................................ 424/263; 260/296 R
[58] Field of Search .......................... 260/296 R, 309; 424/263

[56] References Cited

U.S. PATENT DOCUMENTS 3,691,178  9/1972  Baldwin et al. .................. 260/294.9
3,786,061  1/1974  Novello et al. .................. 260/296 R

FOREIGN PATENT DOCUMENTS 2,061,515  6/1971  Germany ......................... 260/296 R

OTHER PUBLICATIONS

Hofmann, Imidazole and Its Derivatives, Part I, frontispage, pp. 111 to 117 and 119 to 120, Interscience Publishers Inc NY (1953).

Burger, Medicinal Chemistry, vol. 1, frontispage and pp. 34–35, Interscience Publishers, Inc. (1951).

*Primary Examiner*—John D. Randolph
*Attorney, Agent, or Firm*—Daniel T. Szura; Harry E. Westlake, Jr.

[57] ABSTRACT

Substituted imidazole compounds which are useful as anti-hypertensive agents or as xanthine oxidase inhibitors.

20 Claims, No Drawings

SUBSTITUTED IMIDAZOLE COMPOUNDS AND THERAPEUTIC COMPOSITIONS THEREWITH

This is a continuation of application Ser. No. 421,553, filed Dec. 4, 1973, now abandoned.

The present invention relates to a novel and useful class of componds and the use of the compounds as xanthine oxidase inhibitors or in the treatment of hypertension. More particularly, it relates to substituted imidazole compounds.

It is known in the art that certain imidazole compounds are useful as xanthine oxidase inhibitors or as anti-hypertensive agents. Xanthine oxidase inhibitors are useful in the treatment of gout. See British Pat. No. 1,301,754. The present invention is directed to other substituted imidazole compounds which are also useful as xanthine oxidase inhibitors or in the treatment of hypertension. The present compounds thus serve as alternative compounds for those known in the art.

Accordingly, it is an object of the present invention to provide a novel and useful class of compounds which are active as xanthine oxidase inhibitors or in treating hypertension. A further object is to provide a method of producing such compounds. Another object is to provide a method of treatment for hypertension by the use of the new compounds. A still further object is to provide a method of inhibiting xanthine oxidase by the use of the new compounds. Another object is to provide a novel and useful composition for the treatment of hypertension. A still further object is to provide a novel and useful composition for inhibiting xanthine oxidase. Other objects will become apparent as the description of the invention proceeds.

These objects are accomplished by the present invention which provides a compound of the formula

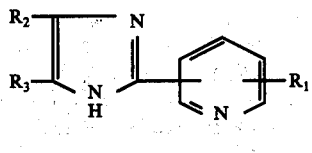

wherein
$R_1$ is hydrogen or alkyl containing 1 to 3 carbon atoms;
$R_2$ is halogen; and
$R_3$ is halogen or $-CF_3$
or a pharmaceutically acceptable salt thereof.

In a preferred embodiment of the present invention, $R_1$ is hydrogen, $R_2$ is chlorine or bromine and $R_3$ is chlorine, bromine or $CF_3$.

The present invention further provides a method of inhibiting xanthine oxidase or lowering blood pressure in an animal which comprises administering to the animal a therapeutically effective amount of a compound of the formula

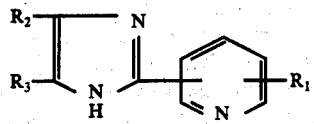

wherein
$R_1$ is hydrogen or alkyl containing 1 to 3 carbon atoms;
$R_2$ is halogen; and
$R_3$ is halogen or $-CF_3$
or a pharmaceutically acceptable salt thereof.

In the treatment of the animal, the compounds of the present invention are generally administered in amounts of from about 0.005 to about 300 mg./kg. of body weight of the animal and preferably from about 0.05 to about 100 mg./kg. In a still more preferred embodiment, the compounds are administered in amounts of from about 0.1 to about 25 mg./kg. of body weight of the animal. In this regard, it should be noted that the dosage must be adjusted depending upon the activity of the compound, the response desired in the animal and also the weight of the animal. In the ranges given above, the more active compounds would tend to be given at the lower dosages and the less active compounds at the higher dosages.

The present invention further provides a pharmaceutical composition comprising an inert pharmaceutically acceptable diluent and a compound of the formula

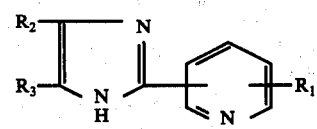

wherein
$R_1$ is hydrogen or alkyl containing 1 to 3 carbon atoms;
$R_2$ is halogen; and
$R_3$ is halogen or $-CF_3$
or a pharmaceutically acceptable salt thereof.

In a single dosage form of the composition of the present invention, the active compound is generally present in the composition in amounts of from about 1 mg. to about 2,000 mgs., more preferably about 5 mgs. to about 1,000 mgs. In a still more preferred embodiment, the active compound is present in amounts of from about 10 mgs. to about 500 mgs. The single dosage form of the compound may be administered in a single slow acting dose or it may be administered in several small doses throughout the day, generally 2 to 8 individual dosages.

The present invention also provides a process for preparing a compound of the formula

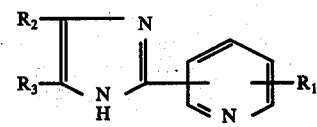

wherein
$R_1$ is hydrogen or alkyl containing 1 to 3 carbon atoms;
$R_2$ is halogen; and
$R_3$ is halogen or $-CF_3$
or a pharmaceutically acceptable salt thereof which comprises reacting a compound of the formula

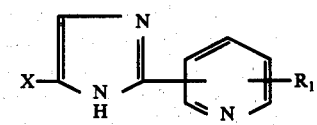

wherein $R_1$ is as defined above and

X is hydrogen or $-CF_3$ or a pharmaceutically acceptable salt thereof with a halogenating agent in an inert solvent.

In a preferred embodiment of the present invention, the reaction is carried out at a temperature of from about $-100°$ C. to about $200°$ C. and more preferable from a temperature of from about $-15°$ C. to about $150°$ C. In actual practice, a temperature of from about $0°$ C. to about $125°$ C. is generally employed since it is easy to accomplish on both a laboratory scale and a commercial scale by the use of ice water or a simple heating system.

The expression "pharmaceutically acceptable salt" is used to mean the non-toxic pharmaceutically acceptable quaternary salts such as the methiodides and ethiodides, and those mineral acid salts such as the hydrochloride salt. The terminology also includes the hydrobromide salt and salts of other inorganic acids. Such salts are well known in the art and would be obvious to the skilled chemist.

The terminology "halogenating agent" is used in its broad sense to mean any chemical compound which will supply the halogen atom in the reaction. In a preferred embodiment of the present invention, the halogenating agent is a "positive halogen" compound or a "positive halogen" donor which supplies bromine, iodine or chlorine in a plus valence state. The various materials which will supply "positive halogen" are well known in the art [see Fresenius "Angewandte Chemie" (1952) pages 470–478 and Arotsky et al "Quarterly Reviews" Volume 16 (1962) pages 282-297] and include the hypohalous acids, the alkali and alkaline-earth metal hypochlorites such as sodium hypochlorite, potassium hypochlorite, calcium hypochlorite and the like. Free halogens such as $Cl_2$, $Br_2$, and $I_2$ will also furnish positive halogen as does chloramine. Another source of "positive halogen" is the N-haloamides such as N-chloroacetamide, N-chlorosuccinimide, N-chlorocaprolactam, N-chlorourea, N-chlorohydantoin as well as the N-bromo and N-iodo analogues of these compounds. All of these materials are well known. However, when using sources of "positive halogen" which are unstable in aqueous systems such as pyridinium perbromide and the alkyl hypochlorites such as t-butyl hypochlorite, inert organic solvents such as dioxane, hexane, chloroform, carbon tetrachloride and alkanols are utilized. The expression "inert solvent" merely signifies a liquid in which the reaction can be carried out without the liquid interfering with the reaction. The terminology includes the above-mentioned solvents as well as many others which would be obvious to the chemist.

The compounds of the present invention can be used in the form of compositions preferably administered in unit dosage form such as tablets, pills, capsules, powders, granules, sterile parenteral solutions or suspensions, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums and fractionally similar materials as pharmaceutical diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The compounds are also useful when administered in the form of suppositories or with a penetrant such as dimethyl sulfoxide.

The liquid forms in which the novel composition of the present invention may be incorporated for administration include suitably flavored emulsions with edible oils, such as cottonseed oil, sesame oil, coconut oil, peanut and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, gelatin and the like. Sterile suspensions or solutions are required for parenteral use. Isotonic preparations containing suitable preservatives are also highly desirable for injection use.

The term single dosage as used in the specification refers to physically discrete units suitable as unitary dosage for warm-blooded animal subjects, each unit containing a predetermined quantity of active material calculated to produce the desired therapeutic effect in association with the required pharmaceutical diluent, carrier or vehicle. The specifications for the novel single dosage forms of this invention are dictated by and are directly dependent on (a) the unique characteristics of the active material and the particular therapeutic effect to be achieved, and (b) the limitations inherent in the art of compounding such an active material for therapeutic use in warm-blooded animals as disclosed in detail in this specification. Examples of suitable oral single dosage forms in accord with this invention are tablets, capsules, pills, powder packets, granules, wafers, cachets, teaspoonfuls, dropperfuls, ampules, vials, segregated multiples of any of the foregoing, and other forms as herein described.

The following examples are given to illustrate the invention and are not intended to limit it in any manner. All parts are given in parts by weight unless otherwise expressed.

EXAMPLE 1

2-(3-Pyridyl)-4,5-dichloroimidazole

To a suspension of 2-(3-pyridyl)-imidazole (1.5 g., 0.01 moles) in chloroform (150 ml.) is added dropwise with stirring over one hour at reflux N-chlorosuccinimide (2.6 g., 0.02 moles). The reaction mixture is heated three hours at reflux. After cooling, the solvent is removed at 20 mm. and the residue triturated with water while heating on a steam bath. The resulting solid is filtered and after recrystallization from acetonitrile 400 mg. of 2-(3-pyridyl)-4,5-dichloroimidazole is obtained, m.p. 237°–238° C.

Anal. calcd.: N, 19.63; C, 44.86; H, 2.35. Found: N, 19.68; C, 45.11; H, 2.38.

EXAMPLE 2

2-(4-Pyridyl)-4(5)-bromo-5(4)-trifluoromethylimidazole

To a suspension of 2-(4-pyridyl)-4-trifluoromethylimidazole (2.1 g., 0.01 moles) in chloroform (100 ml.) is added dropwise with stirring at room temperature bromine (1.6 g., 0.01 moles) in chloroform (5 ml.). The resulting solution is stirred for four hours at room temperature and concentrated at 20 mm. pressure over steam to a solid. Water (25 ml.) is added to the residue. The resulting solution is neutralized with saturated aqueous sodium bicarbonate solution, sodium bisulfite (0.5 g.) is added and the precipitated solid is filtered. After recrystallization from acetonitrile, 1.25 g. of 2-(4-pyridyl)-4(5)-bromo-5(4)-trifluoromethylimidazole is obtained, m.p. 216°–217° C.

Anal. calcd.: N, 14.39; C, 37.01; H, 1.73. Found: N, 14.47, C, 36.93; H, 1.68.

EXAMPLE 3

2-(3-Pyridyl)-4(5)-bromo-5(4)-trifluoromethylimidazole

To a suspension of 2-(3-pyridyl)-4-trifluoromethylimidazole (2.1 g., 0.01 moles) in chloroform (100 ml.) is added dropwise with stirring at room temperature bromine (1.6 g., 0.01 moles) in chloroform (5 ml.). The resulting solution is stirred for four hours at room temperature and concentrated at 20 mm. pressure over steam to a solid. Water (25 ml.) is added to the residue. The resulting solution is neutralized with saturated aqueous sodium bicarbonate solution to yield a solid. After filtration and recrystallization from acetonitrile, 1.15 g. of 2-(3-pyridyl)-4(5)-bromo-5(4)-trifluoromethylimidazole is obtained, m.p. 227°–228° C.

Anal. calcd.: N, 14.39; C, 37.01; H, 1.73. Found: N, 14.35; C, 37.13; H, 1.61.

EXAMPLE 4

2-(3-Pyridyl)-4,5-dibromoimidazole

To a suspension of 2-(3-pyridyl)-imidazole (1.5 g., 0.01 moles) in chloroform (150 ml.) is added dropwise with stirring at room temperature bromine (3.2 g., 0.02 moles) in chloroform (5 ml.). Stirring is continued for 2 hours at room temperature. The chloroform is removed by decantation and the residual material is triturated with water (25 ml.) containing sodium bisulfite (1 g.). The resulting solid is removed by filtration and recrystallized from acetonitrile to yield 0.7 g. of 2-(3-pyridyl)-4,5-dibromoimidazole, m.p. 226°–227° C.

Anal. calcd.: N, 13.87; C, 31.72; H, 1.66. Found: N, 13.77; C, 31.73; H, 1.63.

EXAMPLE 5

2-(2-Methyl-3-pyridyl)-4(5)-bromo-5(4)-trifluoromethylimidazole

The procedure in Example 1 is repeated employing 2-(2-methyl-3-pyridyl)-4-trifluoromethylimidazole (2.27 g., 0.01 moles) in place of 2-(4-pyridyl)-4-trifluoromethylimidazole to obtain 2-(2-methyl-3-pyridyl)-4(5)-bromo-5(4)-trifluoromethylimidazole.

EXAMPLE 6

HARD GELATIN CAPSULES

|  | Gm. |
|---|---|
| 2-(3-pyridyl)-4,5-dichloroimidazole | 200 |
| Cornstarch | 150 |
| Magnesium stearate, powder | 50 |
| Talc | 50 |

The finely powdered ingredients are mixed thoroughly and then encapsulated in 1000 two-piece hard gelatin capsules each containing 200 mgs. of 2-(3-pyridyl)-4,5-dichloroimidazole.

EXAMPLE 7

TABLETS

1000 Tablets each containing 100 mgs. of 2-(4-pyridyl)-4(5)-bromo-5(4)-trifluoromethylimidazole are prepared from the following ingredients:

|  | Gm. |
|---|---|
| 2-(4-pyridyl)-4(5)-bromo-5(4)-trifluoromethylimidazole | 100 |
| Lactose | 50 |
| Starch | 50 |
| Calcium stearate | 10 |
| Talc | 10 |

The finely powdered ingredients are mixed thoroughly and then tableted by a slugging procedure.

EXAMPLE 8

HARD GELATIN CAPSULES

Five thousand two-piece hard gelatin capsules, each containing 400 mg. of 2-(3-pyridyl)-4(5)-bromo-5(4)-trifluoromethylimidazole are prepared from the following ingredients:

|  | Gm. |
|---|---|
| 2-(3-pyridyl)-4(5)-bromo-5(4)-trifluoromethylimidazole | 2000 |
| Lactose | 3000 |
| Magnesium stearate | 1000 |
| Talc | 1000 |

The finely powdered ingredients are mixed thoroughly and then encapsulated by conventional techniques.

EXAMPLE 9

Anti-Hypertensive Activity

The procedure for evaluating the anti-hypertensive activity of the active agents comprises administering the compound either orally or intraperitoneally in spontaneously hypertensive rats of the Wistar-Okamoto strain. Arterial pressure is recorded continuously in these animals through an indwelling aortic catheter introduced through the caudal artery. The animals are allowed free movement in the metabolism cage during the measurements.

When the compounds of the present invention are tested intraperitoneally, distinct anti-hypertensive activity is noted. The compounds also show anti-hypertensive activity when tested orally.

EXAMPLE 10

Xanthine Oxidase Inhibition

For testing purposes, xanthine oxidase obtained from milk may be used to demonstrate the ability of the imidazoles to inhibit the enzyme. The general procedure is to use a 5-10 unit suspension of the enzyme per milliliter of 60% saturated ammonium sulfate; 1 unit of such a suspension converts 1μ mole of xanthine to uric acid per minute. Generally, for a 1-day assay, about 0.05 ml. of enzyme is diluted with about 3 ml. of buffer. As the buffer, tris buffer (bromethamine) (0.05 mole) pH 7.4 may be used. The inhibitor to be tested is dissolved in buffer or a suitable solvent, such as dimethylsulfoxide; the same solvent is used to dilute the solution. The buffer, hypoxanthine and solvent are placed in a cell, and the resulting solution is shaken to absorb air. The diluted enzyme solution is then added, and the rate of increase in absorbance at 290 mμ is noted with a recording spectrophotometer. Generally, sufficient enzyme is used to give about 0.1 absorbance units change per minute, and sufficient inhibitor is used to give 30-70% inhibition. The μM concentration of inhibitor necessary for 50% inhibition ($V_o/V_1 = 2$) is determined by plotting $V_o/V_1$ against I, where $V_o$ = velocity without inhibitor, $V_1$ = velocity with inhibitor, and $I$ = inhibitor concentration. The activity of the tested compound is expressed in terms of percent inhibition. When the compounds of the present invention are tested in the above manner for xanthine oxidase inhibition, distinct activity is noted.

Many other equivalent modifications will be apparent to those skilled in the art from a reading of the foregoing without a departure from the inventive concept.

What is claimed is:

1. A compound of the formula

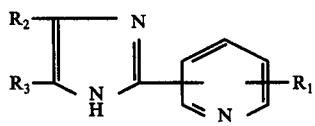

wherein
$R_1$ is hydrogen or alkyl containing 1 to 3 carbon atoms;
$R_2$ is halogen; and
$R_3$ is halogen or —CF$_3$
or a pharmaceutically acceptable salt thereof.

2. A free base of the compound of claim 1.

3. A pharmaceutically acceptable salt of the compound of claim 1.

4. The compound of claim 1 having the formula

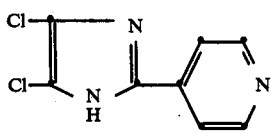

or

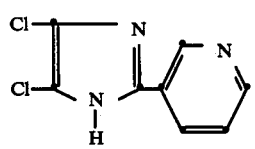

5. The compound of claim 1 having the formula

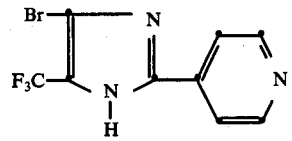

or

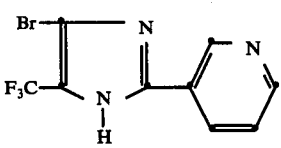

6. The compound of claim 1 having the formula

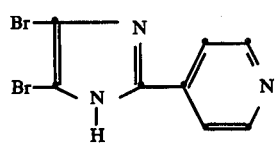

or

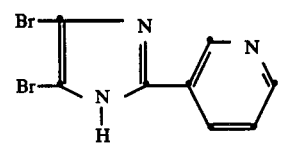

7. A pharmaceutical composition for treating hypertension comprising an inert pharmaceutically acceptable diluent and antihypertensive effective compound of the formula

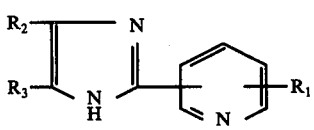

wherein
$R_1$ is hydrogen or alkyl containing 1 to 3 carbon atoms;
$R_2$ is halogen; and
$R_3$ is halogen or —CF$_3$
or a pharmaceutically acceptable salt thereof.

8. The pharmaceutical composition of claim 7 wherein the said compound is present in the composition in amounts of from about 1 mg. to about 2,000 mgs.

9. The pharmaceutical composition of claim 7 wherein the said compound is present in the composition in amounts of from about 5 mgs. to about 1,000 mgs.

10. The pharmaceutical composition of claim 7 wherein said compound is present in the composition in amounts of from about 10 mgs. to about 500 mgs.

11. The pharmaceutical composition of claim 7 wherein $R_2$ and $R_3$ are chlorine.

12. The pharmaceutical composition of claim 7 wherein $R_2$ is bromine and $R_3$ is —CF$_3$.

13. The pharmaceutical composition of claim 7 wherein $R_2$ and $R_3$ are bromine.

14. A pharmaceutical composition for inhibiting xanthine oxidase comprising an inert pharmaceutically acceptable diluent and a xanthine oxidase inhibiting amount of compound of the formula

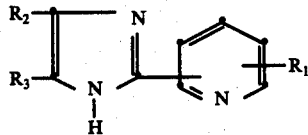

wherein
$R_1$ is hydrogen or alkyl containing 1 to 3 carbon atoms;
$R_2$ is halogen; and
$R_3$ is halogen or $-CF_3$
or a pharmaceutically acceptable salt thereof.

15. The pharmaceutical composition of claim 14 wherein the said compound is present in the composition in amounts of from about 1 mg. to about 2,000 mgs.

16. The pharmaceutical composition of claim 14 wherein the said compound is present in the composition in amounts of from about 5 mgs. to about 1,000 mgs.

17. The pharmaceutical composition of claim 14 wherein the said compound is present in the composition in amounts of from about 10 mgs. to about 500 mgs.

18. The pharmaceutical composition of claim 14 wherein $R_2$ and $R_3$ are chlorine.

19. The pharmaceutical composition of claim 14 wherein $R_2$ is bromine and $R_3$ is $-CF_3$.

20. The pharmaceutical composition of claim 14 wherein $R_2$ and $R_3$ are bromine.